United States Patent [19]

Balogh et al.

[11] Patent Number: 4,559,083

[45] Date of Patent: Dec. 17, 1985

[54] HERBICIDE COMPOSITION CONTAINING CARBOXYLIC-ACID-AMIDOTHIOLCARBAMATE DERIVATIVES

[75] Inventors: Károly Balogh; József Nagy; Zoltán Pintér, all of Miskolc; Csaba Tar, Kazincbarcika; István Tóth, Sajóbábony; Erzsébet Grega née Tóth, Miskolc; Zsolt Dombay, Miskolc; Károly Pásztor, Miskolc; Eszter Urszin née Simon; László Tasi, both of Sajóbábony, all of Hungary

[73] Assignee: Eszakmagyarorszagi Vegyimuvek, Sajóbábony, Hungary

[21] Appl. No.: 421,238

[22] Filed: Sep. 22, 1982

[30] Foreign Application Priority Data

Sep. 29, 1981 [HU] Hungary .............................. 2794/81

[51] Int. Cl.[4] ...................... A01N 37/18; C07C 155/02

[52] U.S. Cl. .......................................... 71/100; 71/88; 260/455 A; 260/239 BF

[58] Field of Search ...................... 71/100; 260/455 A

[56] References Cited

U.S. PATENT DOCUMENTS

| | | | |
|---|---|---|---|
| 3,493,360 | 2/1970 | Fancher et al. | 71/100 |
| 3,897,474 | 7/1975 | Pissioris | 260/455 A |
| 4,108,885 | 8/1978 | Hoyer et al. | 260/455 A |

FOREIGN PATENT DOCUMENTS 52-151146 12/1977 Japan .
53-148530 12/1978 Japan .

OTHER PUBLICATIONS

Chem. Abstracts 89:75452V, (Japanese Patent Application 52 151146) (1978).
Chem. Abstracts 90:181578W, (Japanese Patent Application 53 148530) (1979).

*Primary Examiner*—Catherine L. Mills
*Attorney, Agent, or Firm*—Karl F. Ross; Herbert Dubno

[57] ABSTRACT

The invention relates to a herbicide composition as well as to the preparation of carboxylic-acid-amido-thiolcarbamate derivatives forming the active agent of the composition. The carboxylic acid-amido-thiolcarbamate derivatives are illustrated by general formula (I)

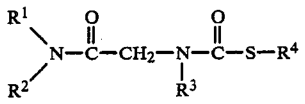

wherein $R_1$ and $R_2$ can be identical or different and can stand for hydrogen, a $C_{1-10}$ straight or branched alkyl group, a $C_{2-10}$ straight or branched alkenyl group, a $C_{5-6}$ cycloalkyl or phenyl group, a phenyl radical substituted by a $C_{1-3}$ alkyl group, a $C_{1-3}$ dialkyl group or halogen, but $R_1$ and $R_2$ can form together a hexamethylene group, too;

$R_2$ can stand for a $C_{1-5}$ straight or branched alkyl radical;

$R_4$ can represent a $C_{1-10}$ straight or branched alkyl group, a $C_{2-10}$ straight or branched alkenyl group, furthermore a phenyl or benzyl radical.

7 Claims, No Drawings

HERBICIDE COMPOSITION CONTAINING CARBOXYLIC-ACID-AMIDOTHIOLCARBAMATE DERIVATIVES

FIELD OF THE INVENTION

The invention relates to a herbicide composition which contains 10 to 80 percent by weight of a carboxylicacid-amido-thiolcarbamate derivative of formula (I)

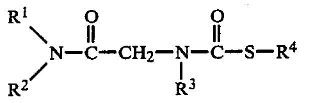

(I)

10 to 90 percent be weight of a solid and/or liquid carrier as well as 1 to 30 percent by weight of an additive, suitably a surface-active agent.

In formula (I) the substituents have the following meanings:

$R^1$ and $R^2$ can be identical or different and can stand for hydrogen,
- a $C_{1-10}$ straight or branched alkyl group,
- a $C_{2-10}$ straight or branched alkenyl group,
- a $C_{5-6}$ cycloalkyl or phenyl group,
- a phenyl radical mono or disubstituted by $C_{1-3}$ alkyl, or by halogen;
- but $R^1$ and $R^2$ can form together a hexamethylene group;

$R^3$ can stand for a $C_{1-5}$ straight or branched alkyl radical;

$R^4$ can represent a $C_{1-10}$ straight or branched alkyl group,
- a $C_{2-10}$ straight or branched alkenyl group,
- a phenyl or a benzyl radical.

BACKGROUND OF THE INVENTION

An indispensable part of modern large-scale plant cultivation is chemical plant protection in which different parasites are prevented from destroying a significant part of the crop and reducing the crop, respectively.

In the past decades several plant protecting agents came into general use which protect the cultivated plants against weed. However, their use resulted in a modification of the weed flora on the one hand, on the other hand in developing resistance individual types of weeds and consequently it was necessary to search for further newer herbicides in order to enable agent rotation and to control the resisting weeds, respectively.

Subsequent to general use of the symmetrical triazines successfully used in the control of dicotyledonous weeds the weed flora shifted to the direction of the monocotyledonous plants and at the beginning of the sixties chloro-acet-anilide-derivatives were employed for protection against them (U.S. Pat. No. 2,863,752). However, the protection against all monocotyledonous weeds, particularly against the resisting *Sorghum halepense,* did not succeed with these compounds (Propachlor, Alachlor and so on).

In the second half of the sixties N,N-disubstituted thiocarbamic type herbicides (U.S. Pat. No. 2,913,327) began to be very much used because of their suitability for the control of several weeds resisting the chloro-acet-anilide-derivatives.

Their use, however, is accompanied by disadvantages because they harm most of the cultivated plants in a dose necessary for a safe weed control to a greater or lesser degree and cause deformed leaves and sprouts.

In order to eliminate this undesired phytotoxic effect combinations of the thiolcarbamates and compounds of so-called antidotal effect were elaborated.

To the thiolcarbamate herbicide some percents of a substance exerting an antidotal effect are admixed and thus the selectivity of the preparation is increased with an unchanged herbicidal effect (Hungarian Patent Specification No. 165,736). However, these substances exerting an antidotal effect do not ensure sufficient protection against the phytotoxic effect of the thiolcarbamates for all cultivated plants and for all types of the individual plants, respectively.

Japanese Patent Specification No. 53-148,530 discloses a thiocarbonyl-amino acid-derivative of a newer structure but these derivatives cannot be used as herbicides, they are suitable only for sterilization.

The glycinethiolcarbamate derivatives disclosed in Japanese Patent Specification No. 52-151,146 have a somewhat similar structure as the above derivatives but these preparations are used in rice cultivations, the phytotoxic effect exerted on other cultivated plant cultures, however, is not known.

All these facts make the research for further new plant protecting agents necessary by which the disadvantages of the agents already used could be eliminated and the agent rotation necessary for safe cultivation could be determined.

DESCRIPTION OF THE INVENTION

In the course of our research work we discovered that the known disadvantages of the thiolcarbamate herbicides can be eliminated if such an agent is used for weed control which contains 10 to 80 percent by weight of a compound of formula (I), 10 to 90 percent by weight of a solid and/or liquid diluting agent as well as 1 to 30 percent by weight of an additive.

The substituents are as defined as follows in the formula (I) of the carboxylic acid-amido-substituted-thiolcarbamate derivatives:

$R^1$ and $R^2$ can be identical or different and can stand for hydrogen, a $C_{1-10}$ straight or branched alkyl group, a $C_{2-10}$ straight or branched alkenyl group, a $C_{5-6}$ cycloalkyl or phenyl group, a phenyl radical mono or disubstituted by $C_{1-3}$ alkyl or halogen, or $R^1$ and $R^2$ together can form a hexamethylene group: $R^3$ can stand for a $C_{1-5}$ straight or branched alkyl radical, $R^4$ can represent a $C_{1-10}$ straight or branched alkyl group, a $C_{2-10}$ straight or branched alkenyl group, a phenyl or benzyl radical.

The solid and/or liquid diluting agent preferably makes up between 20 and 90% of the composition by weight. Preferred liquid diluents include solvents not miscible with water, preferably aromatic or halogenated hydrocarbons. An artificial white oil fraction is a preferred liquid diluent. As preferred solid diluents preferably artificial amorphous silicic acid may be employed as well as minerals of the silicate, sulfate type.

The additive is present in an amount of 1 to 30% by weight of the composition and preferably is present in an amount of 1 to 15% by weight of the composition. The additive is preferably a surface active agent (e.g. a wetting or dispersing agent). Preferred surface active agents include anionic, cationic and non-ionic tensides.

The product of the invention can successfully be used for the control of mono- and dicotyledonous weeds, at the same time it does not exert a harmful effect on cultivated plants. In certain cases a stimulating effect on the green mass of cultivated plants was observed.

The present invention relates to a process for the preparation of carboxylic acid-amido-substituted-thiolcarbamates of formula (I). Accordingly one proceeds so that the N-substituted-amino-carboxylic acid-N,'N'-disubstituted-acid amide thereof of formula (II)

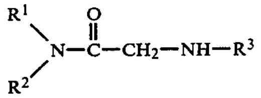

(II)

wherein the substituents are as defined above—is reacted, optionally in a medium containing a solvent in the presence of an acid binding agent with the substituted chloro-formic acid-thiol-ester of formula (III)

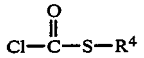

(III)

at a temperature of 20° to 60° C.

SPECIFIC EXAMPLES

The preparation of some compounds of formula (I) is illustrated with the aid of the following examples.

EXAMPLE 1

Into a round-bottom flask provided with a mixer, a thermometer and a feeder and a capacity of 500 ml of 21.4 g of N-ethyl-N-(N'-ethyl-acetanilide)-amine are weighed and under stirring dissolved in 150 ml of benzene. 16 ml of triethylamine are added, then keeping the temperature at 30° to 40° C., 13 g of chloro-formic acid-ethyl-thiolester are added within half an hour. After finishing the addition the reaction mixture is still stirred for half an hour, then 150 ml of distilled water are added. After stirring the organic phase is separated from the aqueous phase. The phase containing an organic solvent is washed at first with dilute hydrochloric acid, then with distilled water.

After the separation from the aqueous phase the phase containing the organic solvent is dried over sodium sulfate, the solvent is evaporated. 20.5 g of N-ethyl-N-(N'-ethyl-acet-anilido)-S-ethyl-thiolcarbamate are obtained in form of a transparent liquid, the refractive index of which is $n_D^{20}=1.5344$.

Yield: 72%. Purity (gas chromatography): 94.8 Wt. %.

EXAMPLE 2

Into a round-bottom flask provided with a mixer, a thermometer and a feed funnel 22.2 g of N-ethyl-N-(N'-isopropyl-acet-anilide)-amine are weighed, under stirring 150 ml of triethylamine are added. Then at a temperature of 30° to 40° C., 13 g of chloro-formic acid-ethyl-thiolester are dropped in under stirring within 30 minutes. After the addition the reaction mixture is still stirred at room temperature for 15 minutes, then 200 ml of water are added. After stirring the organic phase is separated from the aqueous phase, it is washed first with dilute hydrochloric acid, then with distilled water and taken up with 200 ml of benzene. After the evaporation of the solvent 16.5 g of crystalline N-ethyl-N-(N'-isopropyl-acet-anilido)-S-ethyl-thiolcarbamate are obtained which melts at a temperature of 72°-73.5° C.

Yield: 56%. Purity (gas chromatography): 98.2 wt %.

EXAMPLE 3

Into a round-bottom flask provided with a mixer, a thermometer, a dropping funnel and a capacity of 500 ml 10.3 g of N-isopropyl-N-(N'-methyl-acet-anilide)-amine are weighed, then dissolved in 100 ml of toluene. 7 g of chloroformic acid-n-amyl-thiolester are added to the solution under stirring at a temperature of 20° to 40° C. and the reaction mixture is stirred at room temperature for two hours. The reaction mixture is washed first with dilute hydrochloric acid, then with distilled water. The organic phase is separated and dehydrated with sodium sulfate, the toluene is distilled off. 15.2 g of liquid N-isopropyl-N-(N'-methyl-acet-anilido)-S-n-amyl-thiolcarbamate are obtained the refractive index of which is $n_D^{20}=1.5332$.

Yield: 92%. Purity (gas chromatography) 94.5 Wt. %.

EXAMPLE 4

Into a round-bottom flask provided with a mixer, a thermometer and a dropping funnel and a capacity of 500 ml 21.9 g of N-ethyl-N-(2'-methyl-6'-ethyl-acet-anilide)-amine are weighed, then 120 ml of triethylamine are added. Under stirring 22.8 g of chloro-formic acid-n-octyl-thiolester are added to the mixture at a temperature of 20°-25° C., then it is stirred for another three hours. The precipitated solid crystalline material is separated by filtration, washed with n-pentane and dried. 28.5 g of solid, crystalline N-ethyl-N-(2'-methyl-6'-ethyl-acet-anilido)-S-n-octyl-thiolcarbamate are obtained, the melting point of which is 76° to 78.5° C.

Yield: 74%. Purity (gas chromatography): 95.4 Wt. %.

The physical constants of the derivatives of formula (I) prepared with the process according to the invention, similarly as described in Examples 1 to 4 are included in the following Table 1.

TABLE I

| Nr. | substituent | | | | physical constant | |
|---|---|---|---|---|---|---|
| | $R^1$ | $R^2$ | $R^3$ | $R^4$ | m.p. °C. | $n_D^{20}$ |
| 1 | 2 | 3 | 4 | 5 | 6 | 7 |
| 1 | ethyl- | phenyl- | methyl- | ethyl- | — | 1.5127 |
| 2 | i-propyl- | phenyl- | methyl- | ethyl- | 71-72 | — |
| 3 | methyl- | phenyl- | ethyl- | ethyl- | — | 1.5247 |
| 4 | ethyl- | phenyl- | ethyl- | ethyl- | — | 1.5344 |
| 5 | i-propyl- | phenyl- | ethyl- | ethyl- | 72-73.5 | — |
| 6 | methyl- | phenyl- | n-propyl- | ethyl- | — | 1.5415 |
| 7 | ethyl- | phenyl- | n-propyl- | ethyl- | — | 1.5269 |
| 8 | i-propyl- | phenyl- | n-propyl- | ethyl- | 81-83 | — |
| 9 | methyl- | phenyl- | i-propyl- | ethyl- | — | 1.5423 |
| 10 | ethyl- | phenyl- | i-propyl- | ethyl- | — | 1.5259 |
| 11 | i-propyl- | phenyl- | i-propyl- | ethyl- | 96-98 | — |
| 12 | methyl- | phenyl- | allyl- | ethyl- | — | 1.5397 |

TABLE I-continued

| | substituent | | | | physical constant | |
|---|---|---|---|---|---|---|
| Nr. | $R^1$ | $R^2$ | $R^3$ | $R^4$ | m.p. °C. | $n_D^{20}$ |
| 1 | 2 | 3 | 4 | 5 | 6 | 7 |
| 13 | ethyl- | phenyl- | allyl- | ethyl- | — | 1.5309 |
| 14 | i-propyl- | phenyl- | allyl- | ethyl- | 77–78 | — |
| 15 | methyl- | phenyl- | n-butyl- | ethyl- | — | 1.5293 |
| 16 | ethyl- | phenyl- | n-butyl- | ethyl- | — | 1.5284 |
| 17 | i-propyl- | phenyl- | n-butyl- | ethyl- | 73.5–75 | — |
| 18 | methyl- | phenyl- | i-butyl- | ethyl- | — | 1.5276 |
| 19 | ethyl- | phenyl- | i-butyl- | ethyl- | — | 1.5233 |
| 20 | i-propyl- | phenyl- | i-butyl- | ethyl- | 98–99.5 | — |
| 21 | methyl- | phenyl- | s-butyl- | ethyl- | — | 1.5367 |
| 22 | ethyl- | phenyl- | s-butyl- | ethyl | — | 1.5281 |
| 23 | i-propyl- | phenyl- | s-butyl- | ethyl- | 79–81 | — |
| 24 | methyl- | phenyl- | t-butyl- | ethyl- | — | 1.5187 |
| 25 | ethyl- | phenyl- | t-butyl- | ethyl- | — | 1.5198 |
| 26 | i-propyl- | phenyl- | t-butyl- | ethyl- | 64.5–66 | — |
| 27 | methyl- | phenyl- | ethyl- | n-propyl- | — | 1.5177 |
| 28 | ethyl- | phenyl- | ethyl- | n-propyl- | — | 1.5355 |
| 29 | i-propyl- | phenyl- | ethyl- | n-propyl- | 65–67 | — |
| 30 | methyl- | phenyl- | n-propyl- | n-propyl- | — | 1.5307 |
| 31 | ethyl- | phenyl- | n-propyl- | n-propyl- | — | 1.5301 |
| 32 | i-propyl- | phenyl- | n-propyl- | n-propyl- | 61–64 | — |
| 33 | methyl- | phenyl- | i-propyl- | n-propyl- | — | 1.5373 |
| 34 | ethyl- | phenyl- | i-propyl- | n-propyl- | — | 1.5219 |
| 35 | i-propyl- | phenyl- | i-propyl- | n-propyl- | 69–71 | — |
| 36 | methyl- | phenyl- | allyl- | n-propyl- | — | 1.5426 |
| 37 | ethyl- | phenyl- | allyl- | n-propyl- | — | 1.5363 |
| 38 | i-propyl- | phenyl- | allyl- | n-propyl- | 64–66 | — |
| 39 | methyl- | phenyl- | n-butyl- | n-propyl- | — | 1.5323 |
| 40 | ethyl- | phenyl- | n-butyl- | n-propyl- | — | 1.5304 |
| 41 | i-propyl- | phenyl- | n-butyl- | n-propyl | 53–57 | — |
| 42 | methyl- | phenyl- | i-butyl- | n-propyl- | — | 1.5341 |
| 43 | ethyl- | phenyl- | i-butyl- | n-propyl- | — | 1.5287 |
| 44 | i-propyl- | phenyl- | i-butyl- | n-propyl- | 68–71 | — |
| 45 | methyl- | phenyl- | s-butyl- | n-propyl- | — | 1.5366 |
| 46 | ethyl- | phenyl- | s-butyl- | n-propyl- | — | 1.5283 |
| 47 | i-propyl- | phenyl- | s-butyl- | n-propyl- | — | 1.5268 |
| 48 | methyl- | phenyl- | t-butyl- | n-propyl- | — | 1.5355 |
| 49 | ethyl- | phenyl- | t-butyl- | n-propyl- | — | 1.5170 |
| 50 | i-propyl- | phenyl- | t-butyl- | n-propyl- | — | 1.5278 |
| 51 | ethyl- | phenyl- | ethyl- | s-butyl- | — | 1.5239 |
| 52 | i-propyl- | phenyl- | ethyl- | s-butyl- | 68–70 | — |
| 53 | methyl- | phenyl- | n-propyl- | s-butyl- | — | 1.5334 |
| 54 | ethyl- | phenyl- | n-propyl- | s-butyl- | 54–56 | — |
| 55 | i-propyl- | phenyl- | n-propyl- | s-butyl- | 101–103 | — |
| 56 | methyl- | phenyl- | i-propyl- | s-butyl- | — | 1.5323 |
| 57 | ethyl- | phenyl- | i-propyl- | s-butyl- | — | 1.5303 |
| 58 | i-propyl- | phenyl- | i-propyl- | s-butyl- | 58–62 | — |
| 59 | methyl- | phenyl- | allyl- | s-butyl- | — | 1.5400 |
| 60 | ethyl- | phenyl- | allyl- | s-butyl- | — | 1.5361 |
| 61 | i-propyl- | phenyl- | allyl- | s-butyl- | 72–75 | — |
| 62 | methyl- | phenyl- | n-butyl- | s-butyl- | — | 1.5308 |
| 63 | ethyl- | phenyl- | n-butyl- | s-butyl- | — | 1.5255 |
| 64 | i-propyl- | phenyl- | n-butyl- | s-butyl- | 77–78 | — |
| 65 | ethyl- | phenyl- | s-butyl- | s-butyl- | — | 1.5273 |
| 66 | methyl- | phenyl- | t-butyl- | s-butyl- | — | 1.5287 |
| 67 | ethyl- | phenyl- | t-butyl- | s-butyl- | — | 1.5231 |
| 68 | i-propyl- | phenyl- | t-butyl- | s-butyl- | — | 1.5213 |
| 69 | methyl- | phenyl- | n-propyl- | n-amyl- | — | 1.5302 |
| 70 | ethyl- | phenyl- | n-propyl- | n-amyl- | — | 1.5258 |
| 71 | i-propyl- | phenyl- | n-propyl- | n-amyl- | 58–61 | — |
| 72 | methyl- | phenyl- | i-propyl- | n-amyl- | — | 1.5332 |
| 73 | ethyl- | phenyl- | i-propyl- | n-amyl- | — | 1.5270 |
| 74 | i-propyl- | phenyl- | i-propyl- | n-amyl- | — | 1.5242 |
| 75 | methyl- | phenyl- | allyl- | n-amyl- | — | 1.5384 |
| 76 | ethyl- | phenyl- | allyl- | n-amyl- | — | 1.5328 |
| 77 | i-propyl- | phenyl- | allyl- | n-amyl- | — | 1.5293 |
| 78 | methyl- | phenyl- | n-butyl- | n-amyl- | — | 1.5270 |
| 79 | ethyl- | phenyl- | n-butyl- | n-amyl- | — | 1.5234 |
| 80 | i-propyl- | phenyl- | n-butyl- | n-amyl- | 38–40 | — |
| 81 | ethyl- | phenyl- | i-butyl- | n-amyl- | — | 1.5268 |
| 82 | methyl- | phenyl- | t-butyl- | n-amyl- | — | 1.5248 |
| 83 | ethyl- | phenyl- | ethyl- | n-amyl- | — | 1.5281 |
| 84 | i-propyl- | phenyl- | i-butyl- | n-amyl- | — | 1.5190 |
| 85 | methyl- | phenyl- | n-propyl- | i-amyl- | — | 1.5308 |
| 86 | ethyl- | phenyl- | n-propyl- | i-amyl- | — | 1.5262 |
| 87 | i-propyl- | phenyl- | n-propyl- | i-amyl- | 61–64 | — |
| 88 | methyl- | phenyl- | i-propyl- | i-amyl- | — | 1.5329 |
| 89 | ethyl- | phenyl- | i-propyl- | i-amyl- | — | 1.5279 |
| 90 | i-propyl- | phenyl- | i-propyl- | i-amyl- | — | 1.5244 |
| 91 | methyl- | phenyl- | allyl- | i-amyl- | — | 1.5375 |

TABLE I-continued

| | substituent | | | | physical constant | |
|---|---|---|---|---|---|---|
| Nr. | $R^1$ | $R^2$ | $R^3$ | $R^4$ | m.p. °C. | $n_D^{20}$ |
| 1 | 2 | 3 | 4 | 5 | 6 | 7 |
| 92 | ethyl- | phenyl- | allyl- | i-amyl- | — | 1.5322 |
| 93 | i-propyl- | phenyl- | allyl- | i-amyl- | — | 1.5290 |
| 94 | methyl- | phenyl- | n-butyl- | i-amyl- | — | 1.5252 |
| 95 | ethyl- | phenyl- | n-butyl- | i-amyl- | — | 1.5235 |
| 96 | i-propyl- | phenyl- | n-butyl- | i-amyl- | — | 1.5264 |
| 97 | ethyl- | phenyl- | t-butyl- | i-amyl- | — | 1.5257 |
| 98 | methyl- | phenyl- | t-butyl- | i-amyl- | — | 1.5267 |
| 99 | ethyl- | phenyl- | ethyl- | i-amyl- | — | 1.5258 |
| 100 | i-propyl- | phenyl- | t-butyl- | i-amyl- | — | 1.5260 |
| 101 | hydrogen | 2,6-dimethylphenyl- | ethyl- | ethyl- | 107-110 | — |
| 102 | hydrogen | 2,6-dimethylphenyl- | n-propyl- | ethyl- | 83-85 | — |
| 103 | hydrogen | 2,6-dimethylphenyl- | i-propyl- | ethyl- | 126-128 | — |
| 104 | hydrogen | 2,6-dimethylphenyl- | allyl- | ethyl- | 103-104.5 | — |
| 105 | hydrogen | 2,6-dimethylphenyl- | n-butyl- | ethyl- | 92-95 | — |
| 106 | hydrogen | 2,6-dimethylphenyl- | s-butyl- | ethyl- | 112-114.5 | — |
| 107 | hydrogen | 2,6-dimethylphenyl- | t-butyl- | ethyl- | 94.5-96.5 | — |
| 108 | hydrogen | 2,6-dimethylphenyl- | ethyl- | i-propyl- | 91-93 | — |
| 109 | hydrogen | 2,6-dimethylphenyl- | n-propyl- | i-propyl- | 56-63 | — |
| 110 | hydrogen | 2,6-dimethylphenyl- | i-propyl- | n-propyl- | 112-114 | — |
| 111 | hydrogen | 2,6-dimethylphenyl- | allyl- | n-propyl- | 111-112.5 | — |
| 112 | hydrogen | 2,6-dimethylphenyl- | n-butyl- | n-propyl- | 82-84 | — |
| 113 | hydrogen | 2,6-dimethylphenyl- | s-butyl- | n-propyl- | 71-74 | — |
| 114 | hydrogen | 2,6-dimethylphenyl- | t-butyl- | n-propyl- | 154-157 | — |
| 115 | hydrogen | 2,6-dimethylphenyl- | ethyl- | n-octyl- | 66-69 | — |
| 116 | hydrogen | 2,6-dimethylphenyl- | n-propyl- | n-octyl- | 57-61 | — |
| 117 | hydrogen | 2,6-dimethylphenyl- | i-propyl- | n-octyl- | 53-57.5 | — |
| 118 | hydrogen | 2,6-dimethylphenyl- | allyl- | n-octyl- | 69-72 | — |
| 119 | hydrogen | 2,6-dimethylphenyl- | n-butyl- | n-octyl- | 68-70 | — |
| 120 | hydrogen | 2,6-dimethylphenyl- | s-butyl- | n-octyl- | — | 1.5158 |
| 121 | hydrogen | 2,6-dimethylphenyl- | t-butyl- | n-octyl- | 56-63 | — |
| 122 | hydrogen | 2,6-diethylphenyl- | ethyl- | ethyl- | 110-114 | — |
| 123 | hydrogen | 2,6-diethylphenyl- | n-propyl- | ethyl- | 104-108 | — |
| 124 | hydrogen | 2,6-diethylphenyl- | i-propyl- | ethyl- | 130-135 | — |
| 125 | hydrogen | 2,6-diethylphenyl- | allyl- | ethyl- | 125-129 | — |
| 126 | hydrogen | 2,6-diethylphenyl- | n-butyl- | ethyl- | 105-108 | — |
| 127 | hydrogen | 2,6-diethylphenyl- | s-butyl- | ethyl- | 78-82 | — |
| 128 | hydrogen | 2,6-diethylphenyl- | t-butyl- | ethyl- | 200-205 | — |
| 129 | hydrogen | 2,6-diethylphenyl- | ethyl- | n-propyl- | 82-84.5 | — |
| 130 | hydrogen | 2,6-diethylphenyl- | n-propyl- | n-propyl- | 108-112 | — |
| 131 | hydrogen | 2,6-diethylphenyl- | i-propyl- | n-propyl- | 107-109 | — |
| 132 | hydrogen | 2,6-diethylphenyl- | allyl- | n-propyl- | 105-108 | — |
| 133 | hydrogen | 2,6-diethylphenyl- | n-butyl- | n-propyl- | 98-100 | — |
| 134 | hydrogen | 2,6-diethylphenyl- | s-butyl- | n-propyl- | 73-75 | — |
| 135 | hydrogen | 2,6-diethylphenyl- | t-butyl- | n-propyl- | 91-94 | — |
| 136 | hydrogen | 2,6-diethylphenyl- | ethyl- | n-octyl- | 74-75.5 | — |
| 137 | hydrogen | 2,6-diethylphenyl- | n-propyl- | n-octyl- | 60-64 | — |
| 138 | hydrogen | 2,6-diethylphenyl- | i-propyl- | n-octyl- | 63.5-65 | — |
| 139 | hydrogen | 2,6-diethylphenyl- | allyl- | n-octyl- | 70-72 | — |
| 140 | hydrogen | 2,6-diethylphenyl- | n-butyl- | n-octyl- | 54-57 | — |
| 141 | hydrogen | 2,6-diethylphenyl- | s-butyl- | n-octyl- | — | 1.5192 |
| 142 | hydrogen | 2,6-diethylphenyl- | t-butyl- | n-octyl- | 53-55.5 | — |
| 143 | hydrogen | 2-methyl-6-ethylphenyl- | ethyl- | ethyl- | 88-92 | — |
| 144 | hydrogen | 2-methyl-6-ethylphenyl- | n-propyl- | ethyl- | 94-95 | — |
| 145 | hydrogen | 2-methyl-6-ethylphenyl- | i-propyl- | ethyl- | 99-100.5 | — |
| 146 | hydrogen | 2-methyl-6-ethylphenyl- | allyl- | ethyl- | 81.5-82 | — |
| 147 | hydrogen | 2-methyl-6-ethylphenyl- | n-butyl- | ethyl- | 85-90 | — |
| 148 | hydrogen | 2-methyl-6-ethylphenyl- | s-butyl- | ethyl- | — | 1.5257 |
| 149 | hydrogen | 2-methyl-6-ethylphenyl- | t-butyl- | ethyl- | 99.5-100.5 | — |
| 150 | hydrogen | 2-methyl-6-ethylphenyl- | ethyl- | n-propyl- | 60-64 | — |
| 151 | hydrogen | 2-methyl-6-ethylphenyl- | n-propyl- | n-propyl- | 91.5-94 | — |
| 152 | hydrogen | 2-methyl-6-ethylphenyl- | i-propyl- | n-propyl- | 84-87 | — |
| 153 | hydrogen | 2-methyl-6-ethylphenyl- | allyl- | n-propyl- | 104-106 | — |
| 154 | hydrogen | 2-methyl-6-ethylphenyl- | n-butyl- | n-propyl- | 97-99.5 | — |
| 155 | hydrogen | 2-methyl-6-ethylphenyl- | s-butyl- | n-propyl- | — | 1.5233 |
| 156 | hydrogen | 2-methyl-6-ethylphenyl- | t-butyl- | n-propyl- | 121-123 | — |
| 157 | hydrogen | 2-methyl-6-ethylphenyl- | ethyl- | n-octyl- | 73.5-75 | — |
| 158 | hydrogen | 2-methyl-6-ethylphenyl- | n-propyl- | n-octyl- | 60-64 | — |
| 159 | hydrogen | 2-methyl-6-ethylphenyl- | i-propyl- | n-octyl- | — | 1.5192 |
| 160 | hydrogen | 2-methyl-6-ethylphenyl- | allyl- | n-octyl- | 60.5-63.5 | — |
| 161 | hydrogen | 2-methyl-6-ethylphenyl- | n-butyl- | n-octyl- | 50-52 | — |
| 162 | hydrogen | 2-methyl-6-ethylphenyl- | s-butyl- | n-octyl- | — | 1.5205 |
| 163 | hydrogen | 2-methyl-6-ethylphenyl- | t-butyl- | n-octyl- | — | 1.5157 |
| 164 | methyl | phenyl | methyl- | ethyl- | — | 1.5130 |
| 165 | ethyl- | phenyl | ethyl- | n-octyl- | — | 1.5085 |
| 166 | methyl | phenyl | ethyl- | n-octyl- | — | 1.5028 |
| 167 | ethyl- | phenyl | methyl- | n-propyl | — | 1.5403 |
| 168 | methyl | phenyl | methyl- | n-propyl | — | 1.5515 |
| 169 | ethyl- | phenyl | ethyl- | allyl- | — | 1.5497 |
| 170 | ethyl- | phenyl | ethyl- | benzyl- | — | 1.5615 |

TABLE I-continued

| | substituent | | | | physical constant | |
|---|---|---|---|---|---|---|
| Nr. | $R^1$ | $R^2$ | $R^3$ | $R^4$ | m.p. °C. | $n_D^{20}$ |
| 1 | 2 | 3 | 4 | 5 | 6 | 7 |
| 171 | ethyl- | phenyl- | ethyl- | phenyl- | — | 1.5664 |
| 172 | hydrogen | phenyl- | ethyl- | ethyl- | — | 1.5697 |
| 173 | hydrogen | 3-chloro-phenyl- | ethyl- | ethyl- | — | 1.5716 |
| 174 | hydrogen | 3-methyl-phenyl- | ethyl- | ethyl- | — | 1.5675 |
| 175 | hydrogen | cyclohexyl- | ethyl- | ethyl- | 85-88 | — |
| 176 | methyl- | cyclohexyl- | ethyl- | ethyl- | — | 1.5191 |
| 177 | ethyl- | cyclohexyl- | ethyl- | ethyl- | — | 1.5154 |
| 178 | hexamethylene | | ethyl- | ethyl- | 38-42 | — |
| 179 | hexamethylene | | ethyl- | n-propyl- | — | 1.5221 |
| 180 | methyl- | methyl- | ethyl- | ethyl- | — | 1.4980 |
| 181 | ethyl- | ethyl- | ethyl- | ethyl- | — | 1.5015 |
| 182 | ethyl- | ethyl- | ethyl- | n-propyl- | — | 1.4987 |
| 183 | n-propyl- | n-propyl- | ethyl- | ethyl- | 36.5-38.5 | — |
| 184 | allyl- | allyl- | ethyl- | ethyl- | — | 1.5146 |
| 185 | allyl- | allyl- | ethyl- | n-propyl- | — | 1.5119 |
| 186 | i-butyl- | i-butyl- | ethyl- | ethyl- | 58-61 | — |
| 187 | i-butyl- | i-butyl- | i-propyl- | ethyl- | 42-45 | — |

The herbicide according to the invention can be used in form of an emulsion-concentrate, a wettable powder, a granulate, an aqueous or oily suspension in plant protection. The preparation of the product is illustrated by the following examples.

EXAMPLE 5

Into a round-bottom flask provided with a mixer and with a capacity of 500 ml. 50 parts by weight of N-ethyl-N-(N'-ethyl-acet-anilido)-S-ethyl-thiolcarbamate are weighed, 40 parts by weight of kerosine, 5 parts by weight of octyl-phenol-polyglycol-ether (Tensiofix AS) and 5 parts by weight of nonyl-phenyl-polyglycol-ether (Tensiofix IS) emulsifier are added. The stirring is continued until dissolving is finished, thus a 50 Wt.% emulsion concentrate is obtained.

Table II includes the composition data of the emulsifiable concentrates prepared from derivatives of formula (I), similarly as described in Example 5.

TABLE II

| | Components in parts by weight | | | | | | | |
|---|---|---|---|---|---|---|---|---|
| Number according to Table I | compound according to Table I | kerosine | xylene | methylene chloride | phenol | Tensiofix AS | Tensiofix IS | Product |
| 1 | 2 | 3 | 4 | 5 | 6 | 7 | 8 | 9 |
| 1 | 50 | 40 | — | — | — | 5 | 5 | 50 EC |
| 2 | 30 | — | 60 | — | — | 5 | 5 | 30 EC |
| 3 | 50 | 40 | — | — | — | 5 | 5 | 50 EC |
| 4 | 50 | 40 | — | — | — | 5 | 5 | 50 EC |
| 5 | 30 | — | 60 | — | — | 5 | 5 | 30 EC |
| 6 | 50 | 40 | — | — | — | 5 | 5 | 50 EC |
| 7 | 50 | — | 30 | 10 | — | 5 | 5 | 50 EC |
| 8 | 50 | — | 30 | 10 | — | 5 | 5 | 50 EC |
| 9 | 50 | 40 | — | — | — | 5 | 5 | 50 EC |
| 10 | 50 | 40 | — | — | — | 5 | 5 | 50 EC |
| 11 | 20 | — | 52.5 | 17.5 | — | 5 | 5 | 20 EC |
| 12 | 50 | 40 | — | — | — | 5 | 5 | 50 EC |
| 13 | 50 | 40 | — | — | — | 5 | 5 | 50 EC |
| 14 | 20 | — | 52.5 | 17.5 | — | 5 | 5 | 20 EC |
| 15 | 50 | 40 | — | — | — | 5 | 5 | 50 EC |
| 16 | 50 | 40 | — | — | — | 5 | 5 | 50 EC |
| 18 | 50 | 40 | — | — | — | 5 | 5 | 50 EC |
| 19 | 50 | 40 | — | — | — | 5 | 5 | 50 EC |
| 21 | 50 | 40 | — | — | — | 5 | 5 | 50 EC |
| 22 | 50 | 40 | — | — | — | 5 | 5 | 50 EC |
| 23 | 50 | 40 | — | — | — | 5 | 5 | 50 EC |
| 24 | 40 | — | 37.5 | 12.5 | — | 5 | 5 | 40 EC |
| 25 | 50 | 40 | — | — | — | 5 | 5 | 50 EC |
| 27 | 50 | 40 | — | — | — | 5 | 5 | 50 EC |
| 28 | 50 | 40 | — | — | — | 5 | 5 | 50 EC |
| 30 | 50 | 40 | — | — | — | 5 | 5 | 50 EC |
| 31 | 50 | 40 | — | — | — | 5 | 5 | 50 EC |
| 33 | 50 | 40 | — | — | — | 5 | 5 | 50 EC |
| 34 | 50 | — | 30 | 10 | — | 5 | 5 | 50 EC |
| 35 | 50 | — | 20 | — | 20 | 5 | 5 | 50 EC |
| 36 | 50 | 40 | — | — | — | 5 | 5 | 50 EC |
| 37 | 50 | 40 | — | — | — | 5 | 5 | 50 EC |
| 39 | 50 | — | 30 | 10 | — | 5 | 5 | 50 EC |
| 40 | 50 | 40 | — | — | — | 5 | 5 | 50 EC |
| 42 | 50 | — | 30 | 10 | — | 5 | 5 | 50 EC |
| 43 | 50 | — | 30 | 10 | — | 5 | 5 | 50 EC |
| 45 | 50 | 40 | — | — | — | 5 | 5 | 50 EC |
| 46 | 30 | — | 40.5 | 15 | 4.5 | 5 | 5 | 30 EC |
| 47 | 50 | 40 | — | — | — | 5 | 5 | 50 EC |
| 48 | 50 | 40 | — | — | — | 5 | 5 | 50 EC |

TABLE II-continued

| Number according to Table I 1 | Components in parts by weight: compound according to Table I 2 | kerosine 3 | xylene 4 | methylene chloride 5 | phenol 6 | Tensiofix AS 7 | Tensiofix IS 8 | Product 9 |
|---|---|---|---|---|---|---|---|---|
| 49 | 30 | — | 45 | 15 | — | 5 | 5 | 30 EC |
| 50 | 40 | — | 37.5 | 12.5 | — | 5 | 5 | 40 EC |
| 51 | 50 | 40 | — | — | — | 5 | 5 | 50 EC |
| 52 | 40 | — | 22.5 | 25 | 2.5 | 5 | 5 | 40 EC |
| 53 | 50 | 40 | — | — | — | 5 | 5 | 50 EC |
| 54 | 40 | — | 22.5 | 25 | 2.5 | 5 | 5 | 40 EC |
| 56 | 50 | 40 | — | — | — | 5 | 5 | 50 EC |
| 57 | 50 | — | 30 | 10 | — | 5 | 5 | 50 EC |
| 58 | 40 | — | 22.5 | 25 | 2.5 | 5 | 5 | 40 EC |
| 59 | 50 | 40 | — | — | — | 5 | 5 | 50 EC |
| 60 | 50 | 40 | — | — | — | 5 | 5 | 50 EC |
| 62 | 50 | 40 | — | — | — | 5 | 5 | 50 EC |
| 63 | 50 | — | 30 | 10 | — | 5 | 5 | 50 EC |
| 65 | 50 | 40 | — | — | — | 5 | 5 | 50 EC |
| 66 | 50 | 40 | — | — | — | 5 | 5 | 50 EC |
| 67 | 50 | 40 | — | — | — | 5 | 5 | 50 EC |
| 68 | 50 | 40 | — | — | — | 5 | 5 | 50 EC |
| 69 | 50 | 40 | — | — | — | 5 | 5 | 50 EC |
| 70 | 50 | 40 | — | — | — | 5 | 5 | 50 EC |
| 72 | 50 | 40 | — | — | — | 5 | 5 | 50 EC |
| 73 | 50 | 40 | — | — | — | 5 | 5 | 50 EC |
| 74 | 50 | 40 | — | — | — | 5 | 5 | 50 EC |
| 75 | 50 | 40 | — | — | — | 5 | 5 | 50 EC |
| 76 | 50 | 40 | — | — | — | 5 | 5 | 50 EC |
| 77 | 50 | 40 | — | — | — | 5 | 5 | 50 EC |
| 78 | 50 | 40 | — | — | — | 5 | 5 | 50 EC |
| 79 | 50 | 40 | — | — | — | 5 | 5 | 50 EC |
| 81 | 50 | 40 | — | — | — | 5 | 5 | 50 EC |
| 82 | 50 | 40 | — | — | — | 5 | 5 | 50 EC |
| 83 | 50 | 40 | — | — | — | 5 | 5 | 50 EC |
| 84 | 50 | 40 | — | — | — | 5 | 5 | 50 EC |
| 85 | 50 | 40 | — | — | — | 5 | 5 | 50 EC |
| 86 | 50 | 40 | — | — | — | 5 | 5 | 50 EC |
| 88 | 50 | 40 | — | — | — | 5 | 5 | 50 EC |
| 89 | 50 | 40 | — | — | — | 5 | 5 | 50 EC |
| 90 | 50 | 40 | — | — | — | 5 | 5 | 50 EC |
| 91 | 50 | 40 | — | — | — | 5 | 5 | 50 EC |
| 92 | 50 | 40 | — | — | — | 5 | 5 | 50 EC |
| 93 | 50 | 40 | — | — | — | 5 | 5 | 50 EC |
| 94 | 50 | 40 | — | — | — | 5 | 5 | 50 EC |
| 95 | 50 | 40 | — | — | — | 5 | 5 | 50 EC |
| 96 | 50 | — | 30 | 10 | — | 5 | 5 | 50 EC |
| 97 | 50 | 40 | — | — | — | 5 | 5 | 50 EC |
| 98 | 50 | 40 | — | — | — | 5 | 5 | 50 EC |
| 99 | 50 | 40 | — | — | — | 5 | 5 | 50 EC |
| 100 | 50 | 40 | — | — | — | 5 | 5 | 50 EC |

EXAMPLE 6

50 parts by weight of N-ethyl-N-(N'-isopropyl-acetanilido)-S-ethyl-thiolcarbamate, 40 parts by weight of a synthetic amorphous silicic acid grist (Zeolex 444), 4 parts by weight of sulfite waste liquor powder, 2 parts by weight of alkyl-sulfonic acid-sodium (Nettzer IS) wetting agent and 4 parts by weight of sodium-lignin-sulfonate (Hoes 1494) dispersing agent are weighed into a powder mixer, the mixture is ground in an air-flow mill and then homogenized.

A 50 Wt.% wettable powder mixture is obtained.

A wettable powder product can be prepared from the derivatives provided in Table III in a similar way.

TABLE III

| Number according to Table I | components in parts by weight: compound according to Table I | Zeolex 444 | sulfite waste-liquor powder | Nettzer IS | Hoes 1494 | product |
|---|---|---|---|---|---|---|
| 17 | 50 | 40 | 4 | 2 | 4 | 50 WP |
| 20 | 50 | 40 | 4 | 2 | 4 | 50 WP |

TABLE III-continued

| Number according to Table I | components in parts by weight: compound according to Table I | Zeolex 444 | sulfite waste-liquor powder | Nettzer IS | Hoes 1494 | product |
|---|---|---|---|---|---|---|
| 26 | 50 | 40 | 4 | 2 | 4 | 50 WP |
| 29 | 50 | 40 | 4 | 2 | 4 | 50 WP |
| 32 | 50 | 40 | 4 | 2 | 4 | 50 WP |
| 38 | 50 | 40 | 4 | 2 | 4 | 50 WP |
| 41 | 50 | 40 | 4 | 2 | 4 | 50 WP |
| 44 | 50 | 40 | 4 | 2 | 4 | 50 WP |
| 55 | 50 | 40 | 4 | 2 | 4 | 50 WP |
| 61 | 50 | 40 | 4 | 2 | 4 | 50 WP |
| 64 | 50 | 40 | 4 | 2 | 4 | 50 WP |
| 71 | 50 | 40 | 4 | 2 | 4 | 50 WP |
| 80 | 50 | 40 | 4 | 2 | 4 | 50 WP |
| 87 | 50 | 40 | 4 | 2 | 4 | 50 WP |

EXAMPLE 7

80 g of active agent No. 20 of Table I are homogenized with 10 g of synthetic amorphous silicic acid grist, 2 g of an alkyl-sulfonic acid-sodium wetting agent as well as 3 g of cresol-formaldehyde condensate and 5 g of a sodium-lignin-sulfonate dispersing agent. The mixture is preground in a laboratory ball mill for 1 hour, then follows fine grinding with steady addition in a contraplex laboratory rod mill. 100 g of a wettable powder product containing 80 Wt.% of an active agent are obtained.

Floatability (after half an hour): 84%

Wet sieve residue (on a 50μ sieve): 1.4 Wt.%

Bulk density: 0.36 g/$cm^3$.

EXAMPLE 8

65 g of active agent No. 52 of Table I, 10 g of a synthetic amorphous silicic acid grist and 15 g of a mineral kieselguhr carrier, 2 g of an alkyl-sulfonic acid-sodium wetting agent as well as 4 g of cresol-formaldehyde-condensate and 5 g of sodium-lignin-sulfonate dispersing agent are together homogenized. The mixture is preground in a laboratory ball mill for 1 hour, then fine grinding is carried out in an ultraplex beater-disc laboratory mill with steady addition.

100 g of a wettable powder product containing 65 Wt.% of an active agent are obtained.

Floatability: (after half an hour): 86%

Wet sieve residue (on a 50μ sieve): 1.2 Wt.%

Bulk density: 0.32 g/$cm^3$.

EXAMPLE 9

10 g of active agent No. 115 of Table I are thoroughly admixed with 10 g of synthetic amorphous silicic acid grist and 70 g of a mineral kieselguhr carrier, 2 g of an alkyl-sulfonic acid-sodium wetting agent, 4 g of cresol-formaldehyde condensate and 5 g of a sodium-lignin-sulfonate dispersing agent. This mixture is preground in a laboratory ball mill for 1 hour, then fine grinding is performed in an ultraplex beater-disc mill with steady addition.

The obtained wettable powder product containing 10 Wt.% of an active agent has a Floatability (after half an hour): of 92%

Wet sieve residue (on a 50μ sieve): 0.65 Wt.%

Bulk density: 0.26 g/$cm^3$.

EXAMPLE 10

30 g of active agent No. 4 of Table I are admixed with 30 g of xylene by 5 minutes of stirring. The mixture is sprayed on 30 g of ground synthetic amorphous silicic acid carrier (max. corn size: 20μ) in a shaker. 2 g of an alkyl-sulfonic acid-sodium wetting agent, 3 g of cresol-formaldehyde-condensate and 5 g of sodium-lignin-sulfonate dispersing agent are added.

The mixture is homogenized and ground in a laboratory ball mill for 1 hour. A wettable powder product containing 30 Wt.% of an active agent is obtained.

Floatability (after half an hour): 88%

Wet sieve residue (on a 50μ sieve): 0.1 Wt.%

Bulk density: 0.21 g/$cm^3$.

EXAMPLE 11

80 g of active agent No. 4 of Table I, 14 g of kerosine as well as an emulsifier containing the mixture of 6 g of dodecyl-benzene-sulfonic acid-calcium and polyoxy-ethylene-alkyl-phenyl are homogenized with a laboratory mixer for 15 minutes, then filtered on a folder filter. An emulsion concentrate containing 80 Wt.% of an active agent is obtained.

Density: 1.07 g/$cm^3$

Emulsion stability, after 2 and 24 hours some reversible precipitation.

EXAMPLE 12

10 g of active agent No. 11 of Table I are dissolved under stirring in the mixture of 50 g of xylene and 30 g of methylene-chloride. An emulsifier containing the mixture of 10 g of dodecyl-benzene-sulfonic acid-calcium and polyoxy-ethylene-alkyl-phenol is added, the solution is homogenized by stirring for 15 minutes and finally filtered on a folder filter.

An emulsion concentraate containing 10 Wt.% of an active agent is obtained.

Density: 1.02 g/$cm^3$

Emulsion stability: (1 percent concentration, in water of 19.2° GH), after 2 hours stable, after 24 hours min. reversible precipitation.

EXAMPLE 13

20 g of active agent No. 130 of Table I and 20 g of mineral kieselguhr grist are homogenized, then ground in an ultraplex beater-disc mill under a corn size of 40μ. The powder mixture is homogenized with 49 g of gypsum binding agent and pulped with 11 g of a 0.4 Wt.% methyl-cellulose solution. The thick pulp is poured into vaseline oil containing 2000 g of a 0.5 Wt.% polyoxy-ethylene-sorbitane-monooleate wetting agent and granulated under intense stirring. In the course of a 2 hour stirring the binding agent solidifies. The granulate is filtered off the oil, the residual oil is washed off and dried at 50° C. 100 g of a granulate containing 20 Wt.% of an active agent are obtained.

Corn size: 90% between 0.4 and 1.0 mm.

EXAMPLE 14

80 g of active agent No. 144 of Table I, 6 g of a synthetic amorphous silicic acid carrier, 20 g of ethylene-glycol anti-freezer, tenside containing the mixture of 20 g of nonyl-phenol-polyglycol-ether and sodium-oleoyl-methyl-tauride and 74 g of water are weighed into a laboratory pearl mill with a capacity of 0.5 l and 300 g of a glass pearl charge (diameter 1.0 to 1.5 mm) are added. The suspension is ground with a speed of 1000 r.p.m. for 1 hour. The charge is separated from the product on a sieve.

An aqueous suspension concentrate containing 40 Wt.% of an active agent is obtained.

Density: 1.12 g/$cm^3$

Floatability: 95%

Cold resistance: at 0° C. no change within 48 hours.

EXAMPLE 15

40 g of active agent No. 71 of Table I, 140 g of technical vaseline oil and tenside containing the mixture of 20 g of dodecyl-benzene-sulfonic acid-calcium and polyoxy-ethylene-alcohol are weighed into a laboratory pearl mill with a capacity of 0.5 l and 300 g of glass pearl charge with a diameter of 1.0 to 1.5 mm are added. The suspension is ground at a speed of 1000 r.p.m. for 1 hour, then the product is separated from the charge on a sieve. An oily suspension concentrate is obtained. 20 Wt.%.

Density: 0.97 g/$cm^3$

Floatability: (in a 3 percent concentration, after 30 minutes): 98%.

The essence of the recognition of the invention resides in the fact that the mono- and dicotyledonous weeds can be successfully controlled by products containing 10 to 90 Wt.% of a liquid and/or solid diluting agent(s), 10 to 30 Wt.% of an additive(s) and 10 to 80 Wt.% of carboxylic acid-amido-substituted-thiolcarbamates derivatives of formula (I), at the same time the product does not exert any harmful effect on cultivated plants.

The following examples illustrate biological tests carried out with the product according to the invention.

EXAMPLE 16

The test series were carried out in jars with a surface of 120 $cm^2$ and were repeated in parallel four times. 400 g of air-dry sand were weighed into the jars and the seeds of the test plants were sown into the jars.

MvTC-596 maize (*Zea mays*): 15 corns

Ireger striped sunflower (*Helianthus annuus*): 15 corns

K. Jubileum tomato (*Solonum lysopersicum*): 15 corns crowfoot grass (*Echinocloa-crus-galli*): 1 g.

The seeds were covered with 200 g of sand and the soil was treated chemically by spraying. The products according to the invention were used in formulation 50 EC (emulsion concentrate) and 50 WP (wettable powder). For the purpose of comparison treatments were performed with the product 78 EC of EPTC thiolcarbamate and the product 80 Ec containing EPTC as well as the antidote N-dichloro-acetyl-1-oxa-4-aza-spiro-4,5-decane (code AD-67), too.

The dose of every treatment corresponds to an addition of 3 kg of active agent/ha.

After the treatment 100 g of sand were weighed into the jars, the soil was watered up to a water capacity of 65% and in the cours of cultivation a uniform soil wetness was ensured by repeated watering. The plants were cultivated in a glass-house under 400 W daylight lamps of type HgMI/D in a 16 hour lighting period. The daily average temperature was 26.6° C. (min. 24° C., max. 29.2° C.) while the average relative humidity was 73.6%.

For the evaluation of the tests untreated control plants were grown the data of which measured at the evaluation were taken as 100%.

The evaluation was performed in the case of maize, sunflower and crowfoot grass on the 14th day after the treatment, for potatoes on the 19th day by measuring the green mass of the plants. Besides in the case of maize the length of the sprouts was measured, too.

The results of the tests carried out with the products Nos. 1 to 26 according to Tables II and III are shown in Table IV.

TABLE IV

| Treatments | Maize (zea mays) length of sprout % | Maize (zea mays) green weight % | Sunflower green weight % | Tomato green weight % | Echinoclea sp green weight % |
|---|---|---|---|---|---|
| 1 | 2 | 3 | 4 | 5 | 6 |
| Untreated control | 100 | 100 | 100 | 100 | 100 |
| EPTC + AD-67 antid. 80EC | 96 | 97 | 85 | 13 | 0 |
| EPTC 78EC | 57 | 84 | 77 | 11 | 0 |
| Number according to Table I | | | | | |
| 1 | 109 | 91 | 73 | 0 | 0 |
| 2 | 104 | 94 | 93 | 0 | 18 |
| 3 | 103 | 91 | 97 | 0 | 0 |
| 4 | 103 | 91 | 95 | 0 | 0 |
| 5 | 103 | 95 | 80 | 0 | 31 |
| 6 | 108 | 97 | 80 | 47 | 0 |
| 7 | 101 | 83 | 92 | 0 | 0 |
| 8 | 105 | 88 | 90 | 40 | 36 |
| 9 | 110 | 101 | 109 | 74 | 2 |
| 10 | 112 | 101 | 106 | 64 | 2 |
| 11 | 94 | 94 | 122 | 90 | 31 |
| 12 | 88 | 84 | 122 | 44 | 4 |
| 13 | 82 | 82 | 124 | 46 | 0 |
| 14 | 91 | 92 | 94 | 69 | 48 |
| 15 | 96 | 101 | 124 | 54 | 6 |
| 16 | 86 | 86 | 118 | 79 | 7 |
| 17 | 97 | 97 | 93 | 102 | 50 |
| 18 | 109 | 123 | 86 | 82 | 0 |
| 19 | 85 | 82 | 126 | 91 | 4 |
| 20 | 108 | 114 | 104 | 87 | 30 |
| 21 | 106 | 107 | 99 | 65 | 0 |
| 22 | 114 | 120 | 107 | 77 | 3 |
| 23 | 107 | 115 | 103 | 105 | 4 |
| 24 | 99 | 101 | 114 | 87 | 7 |
| 25 | 117 | 129 | 107 | 73 | 2 |
| 26 | 108 | 116 | 120 | 87 | 21 |

From the data of the tests it is clear, that the products of the invention successfully control the crowfoot grass, at the same time they do not harm maize and sunflower, even exert a stimulating effect in most of the cases. Though in the case of tomato individual derivatives reduced the green mass, at the same time other ones showed a stimulating effect, too.

EXAMPLE 17

The effect of products Nos. 27 to 45 of Tables II and III as well as of products containing active agents Nos. 111 to 160 and 164 to 187 of Table I was examined with the test methods described in the previous example with the difference that Hungarian grass (*Setaria* sp was used as test plant.)

The result of the tests are summarized in Table V.

TABLE V

| Treatments | Maize (Zea mays) length of sprout % | Maize (Zea mays) green weight % | Sunflower (Helianthus an) green weight % | Tomato (Solanum lysp.) green weight % | Hungarian Grass (Setarin sp) green weight % |
|---|---|---|---|---|---|
| 1 | 2 | 3 | 4 | 5 | 6 |
| Untreated control | 100 | 100 | 100 | 100 | 100 |
| EPTC + AD-67 80 EC | 94 | 87 | 89.1 | 32.7 | 3.8 |
| EPTC 78EC | 28.6 | 46.9 | 94.8 | 63.6 | 34.6 |
| Number according to Table I | | | | | |
| 27 | 93.8 | 84.5 | 85.7 | 98.2 | 18.6 |
| 28 | 87.0 | 76.9 | 103.3 | 107.3 | 0.0 |
| 29 | 81.9 | 65.2 | 95.1 | 116.4 | 21.3 |

TABLE V-continued

| Treatments 1 | Maize (Zea mays) length of sprout % 2 | Maize (Zea mays) green weight % 3 | Sunflower (Helianthus an) green weight % 4 | Tomato (Solanum lysp.) green weight % 5 | Hungarian Grass (Setarin sp) green weight % 6 |
|---|---|---|---|---|---|
| 30 | 97.5 | 97.2 | 95.5 | 100.0 | 58.3 |
| 31 | 91.1 | 87.3 | 88.4 | 110.9 | 27.3 |
| 32 | 91.9 | 90.9 | 90.1 | 129.1 | 42.3 |
| 33 | 90.4 | 85.3 | 88.0 | 96.4 | 33.2 |
| 34 | 95.8 | 92.2 | 88.5 | 74.5 | 19.8 |
| 35 | 101.7 | 97.8 | 92.3 | 81.8 | 26.3 |
| 36 | 102.5 | 95.4 | 90.7 | 100.0 | 24.5 |
| 37 | 89.0 | 80.8 | 96.0 | 103.6 | 29.1 |
| 38 | 89.2 | 77.1 | 108.6 | 98.2 | 28.7 |
| 39 | 96.2 | 95.4 | 104.6 | 96.4 | 39.1 |
| 40 | 97.0 | 88.8 | 96.2 | 94.5 | 22.7 |
| 41 | 94.3 | 89.9 | 90.8 | 125.5 | 21.5 |
| 42 | 97.1 | 93.3 | 86.0 | 118.2 | 26.6 |
| 43 | 96.7 | 92.4 | 90.2 | 118.2 | 70.0 |
| 44 | 92.1 | 80.7 | 84.7 | 121.8 | 82.8 |
| 45 | 94.5 | 90.5 | 82.6 | 100.0 | 45.1 |
| 111 | 118.6 | 137.9 | 124.2 | 154.4 | 127.3 |
| 112 | 99.8 | 101.4 | 118.9 | 175.4 | 91.2 |
| 113 | 108.7 | 131.2 | 127.4 | 145.1 | 93.2 |
| 114 | 121.2 | 139.7 | 141.5 | 175.7 | 102.7 |
| 115 | 99.5 | 102.5 | 131.4 | 138.4 | 130.6 |
| 116 | 113.3 | 111.9 | 121.2 | 147.4 | 97.5 |
| 117 | 118.9 | 136.0 | 126.2 | 109.6 | 131.8 |
| 118 | 125.4 | 132.9 | 130.0 | 127.7 | 119.9 |
| 119 | 116.3 | 129.4 | 126.1 | 115.8 | 85.6 |
| 120 | 92.1 | 90.7 | 124.0 | 134.3 | 94.0 |
| 121 | 101.7 | 108.1 | 131.3 | 100.0 | 125.0 |
| 122 | 117.5 | 143.7 | 123.0 | 149.9 | 118.0 |
| 123 | 102.5 | 98.6 | 115.7 | 153.6 | 85.0 |
| 124 | 110.6 | 100.8 | 109.9 | 134.2 | 116.0 |
| 125 | 111.8 | 118.0 | 123.4 | 134.3 | 92.4 |
| 126 | 98.6 | 91.4 | 121.2 | 128.5 | 100.8 |
| 127 | 96.6 | 95.1 | 119.4 | 110.6 | 94.5 |
| 128 | 114.3 | 106.2 | 124.8 | 131.0 | 115.8 |
| 129 | 129.9 | 125.4 | 128.9 | 168.5 | 136.5 |
| 130 | 114.5 | 121.9 | 130.4 | 124.5 | 103.9 |
| 131 | 108.1 | 114.1 | 109.6 | 95.0 | 110.1 |
| 132 | 120.7 | 116.1 | 126.6 | 122.9 | 119.9 |
| 133 | 111.3 | 118.9 | 115.5 | 104.8 | 110.1 |
| 134 | 102.7 | 108.6 | 116.9 | 144.1 | 92.9 |
| 135 | 111.3 | 110.9 | 154.5 | 145.7 | 97.1 |
| 136 | 113.2 | 128.7 | 139.0 | 158.9 | 143.1 |
| 137 | 124.6 | 143.9 | 116.1 | 154.4 | 97.5 |
| 138 | 114.7 | 134.3 | 115.3 | 147.4 | 105.7 |
| 139 | 120.8 | 140.0 | 128.3 | 140.9 | 119.3 |
| 140 | 116.7 | 148.0 | 113.4 | 136.9 | 127.9 |
| 141 | 121.4 | 139.2 | 129.6 | 164.4 | 86.4 |
| 142 | 98.6 | 113.6 | 115.5 | 101.8 | 122.4 |
| 143 | 102.8 | 109.8 | 136.1 | 134.3 | 93.8 |
| 144 | 98.2 | 111.2 | 119.4 | 145.8 | 112.7 |
| 145 | 108.3 | 130.6 | 139.2 | 96.5 | 68.4 |
| 146 | 96.3 | 96.5 | 113.3 | 103.9 | 126.9 |
| 147 | 102.1 | 112.9 | 118.6 | 100.0 | 127.5 |
| 148 | 110.6 | 126.9 | 111.9 | 107.1 | 97.5 |
| 149 | 108.3 | 110.9 | 120.9 | 111.1 | 138.6 |
| 150 | 120.8 | 139.8 | 126.4 | 84.2 | 102.0 |
| 151 | 104.3 | 123.1 | 117.6 | 90.7 | 125.2 |
| 152 | 82.0 | 108.0 | 103.4 | 79.0 | 101.4 |
| 153 | 117.1 | 137.9 | 96.4 | 92.1 | 100.0 |
| 154 | 103.9 | 101.2 | 117.1 | 89.5 | 132.2 |
| 155 | 103.9 | 100.9 | 116.4 | 126.1 | 144.4 |
| 156 | 114.9 | 102.7 | 109.4 | 91.6 | 134.1 |
| 157 | 106.7 | 107.7 | 115.1 | 83.5 | 128.7 |
| 158 | 110.2 | 126.2 | 107.0 | 93.0 | 97.5 |
| 159 | 88.2 | 92.6 | 93.0 | 98.3 | 87.3 |
| 160 | 104.5 | 102.4 | 118.9 | 116.3 | 100.4 |
| 164 | 100.3 | 85.9 | 84.1 | 98.3 | 118.3 |
| 165 | 102.1 | 77.7 | 92.7 | — | 109.7 |
| 166 | 102.4 | 83.8 | 90.8 | — | 68.5 |
| 167 | 91.2 | 74.2 | 86.6 | 108.1 | 105.8 |
| 168 | 95.9 | 99.2 | 80.9 | 102.9 | 80.9 |
| 169 | 104.4 | 155.0 | 94.1 | 74.6 | 89.3 |
| 170 | 104.7 | 98.4 | 94.9 | 103.6 | 106.2 |
| 171 | 105.3 | 98.3 | 100.1 | 97.8 | 64.5 |
| 172 | 98.9 | 96.0 | 96.1 | 108.5 | 139.4 |
| 173 | 104.0 | 107.6 | 88.8 | 108.2 | 137.3 |

TABLE V-continued

| Treatments 1 | Maize (Zea mays) length of sprout % 2 | Maize (Zea mays) green weight % 3 | Sunflower (*Helianthus an*) green weight % 4 | Tomato (*Solanum lysp.*) green weight % 5 | Hungarian Grass (Setarin sp) green weight % 6 |
|---|---|---|---|---|---|
| 174 | 103.5 | 100.8 | 92.1 | 118.2 | 137.9 |
| 175 | 95.7 | 90.5 | 84.5 | 144.1 | 134.3 |
| 176 | 95.0 | 84.3 | 94.5 | 169.5 | 121.0 |
| 177 | 107.1 | 98.6 | 90.4 | 97.3 | 74.0 |
| 178 | 98.4 | 85.7 | 86.8 | 111.1 | 76.5 |
| 179 | 92.7 | 81.0 | 92.2 | 124.3 | 35.2 |
| 180 | 92.7 | 80.7 | 97.1 | 114.0 | 111.9 |
| 181 | 88.5 | 79.6 | 90.1 | 109.7 | 92.6 |
| 182 | 92.2 | 63.2 | 92.4 | 112.8 | 30.8 |
| 183 | 98.7 | 84.5 | 81.2 | 100.3 | 98.8 |
| 184 | 105.1 | 93.4 | 81.3 | 133.1 | 76.3 |
| 185 | 89.2 | 76.3 | 86.4 | 100.0 | 10.9 |
| 186 | 106.7 | 78.3 | 92.2 | 95.9 | 132.5 |
| 187 | 100.5 | 85.3 | 89.2 | 107.7 | 98.7 |

EXAMPLE 18

The effect of products Nos. 46 to 100 according to Tables II and III as well as products containing active agents Nos. 101 to 110 of Table I was examined with the test method described in Example 16 with the difference that Hungarian grass (*Setaria* sp) was used as test plant and that the treatments were performed with a dose of 2 kg/ha.

The test results are included in Table VI.

TABLE VI

| Treatments 1 | Maize (Zea mays) length of sprout % 2 | Maize (Zea mays) green weight % 3 | Sunflower (*Helianthus an*) green weight % 4 | Tomato (*Solanum lysp*) green weight % 5 | Hungarian grass (Setaria sp) green weight % 6 |
|---|---|---|---|---|---|
| Untreated control | 100 | 100 | 100 | 100 | 100 |
| EPTC + AD-67 80 EC | 109.3 | 95 | 92.2 | 68.2 | 16.5 |
| EPTC 78 EC | 79.7 | 92.4 | 96.9 | 93.2 | 11.5 |
| Number according to Table I | | | | | |
| 46 | 108.1 | 116.2 | 103.8 | 113.2 | 101.1 |
| 47 | 111.0 | 120.9 | 99.2 | 105.0 | 83.1 |
| 48 | 109.7 | 115.5 | 91.2 | 101.8 | 92.6 |
| 49 | 99.6 | 109.3 | 90.0 | 125.0 | 78.3 |
| 50 | 111.4 | 120.4 | 98.3 | 105.0 | 111.7 |
| 51 | 94.1 | 92.1 | 92.0 | 125.0 | 91.4 |
| 52 | 109.7 | 120.8 | 104.8 | 101.8 | 94.8 |
| 53 | 111.4 | 124.7 | 97.9 | 116.8 | 90.3 |
| 54 | 108.9 | 129.9 | 95.1 | 90.0 | 77.4 |
| 55 | 107.6 | 107.9 | 98.1 | 87.5 | 71.3 |
| 56 | 107.6 | 117.9 | 95.6 | 96.8 | 71.1 |
| 57 | 105.5 | 108.9 | 96.9 | 108.2 | 91.4 |
| 58 | 117.8 | 138.7 | 97.6 | 116.8 | 70.0 |
| 59 | 101.3 | 104.4 | 99.2 | 120.0 | 102.7 |
| 60 | 106.3 | 106.9 | 87.7 | 94.8 | 97.1 |
| 61 | 99.6 | 93.7 | 91.2 | 91.0 | 79.5 |
| 62 | 112.3 | 130.6 | 90.5 | 112.5 | 60.5 |
| 63 | 97.5 | 94.3 | 95.5 | 115.0 | 90.3 |
| 64 | 108.5 | 115.0 | 109.5 | 117.8 | 69.1 |
| 65 | 109.7 | 126.6 | 98.3 | 105.2 | 58.0 |
| 66 | 100.8 | 100.5 | 93.4 | 90.0 | 71.1 |
| 67 | 95.3 | 103.3 | 98.6 | 116.8 | 73.1 |
| 68 | 106.3 | 115.3 | 94.4 | 105.0 | 81.7 |
| 69 | 106.3 | 113.3 | 95.6 | 100.0 | 83.1 |
| 70 | 107.6 | 118.5 | 93.0 | 118.2 | 98.4 |
| 71 | 107.2 | 116.9 | 97.2 | 100.0 | 105.0 |
| 72 | 113.6 | 122.0 | 90.3 | 103.5 | 113.1 |
| 73 | 113.1 | 127.5 | 92.8 | 100.0 | 81.3 |
| 74 | 98.3 | 93.3 | 99.7 | 111.5 | 82.4 |
| 75 | 109.3 | 112.5 | 90.0 | 106.8 | 74.0 |
| 76 | 103.0 | 104.0 | 95.4 | 109.5 | 106.1 |
| 77 | 114.0 | 124.9 | 96.7 | 118.2 | 84.7 |
| 78 | 106.8 | 99.7 | 107.3 | 108.2 | 102.3 |
| 79 | 111.4 | 122.8 | 102.1 | 111.5 | 76.7 |
| 80 | 101.3 | 98.7 | 94.6 | 85.0 | 107.9 |
| 81 | 109.3 | 121.6 | 87.4 | 100.0 | 105.9 |
| 82 | 123.3 | 142.1 | 104.7 | 100.0 | 112.9 |

TABLE VI-continued

| Treatments 1 | Maize (*Zea mays*) length of sprout % 2 | Maize (*Zea mays*) green weight % 3 | Sunflower (*Helianthus an*) green weight % 4 | Tomato (*Solanum lysp*) green weight % 5 | Hungarian grass (Setaria sp) green weight % 6 |
|---|---|---|---|---|---|
| 83 | 108.9 | 119.7 | 95.1 | 101.8 | 109.5 |
| 84 | 113.1 | 115.9 | 107.1 | 80.8 | 23.7 |
| 85 | 105.9 | 103.0 | 89.8 | 91.0 | 58.9 |
| 86 | 106.8 | 110.5 | 95.8 | 95.0 | 56.4 |
| 87 | 105.5 | 115.0 | 89.8 | 86.8 | 73.8 |
| 88 | 97.0 | 97.4 | 81.5 | 105.0 | 84.2 |
| 89 | 105.1 | 110.3 | 82.7 | 97.2 | 67.7 |
| 90 | 99.2 | 92.7 | 100.3 | 95.0 | 61.9 |
| 91 | 108.9 | 100.3 | 80.1 | 91.0 | 72.7 |
| 92 | 106.3 | 113.6 | 100.4 | 100.0 | 54.9 |
| 93 | 99.6 | 89.6 | 80.8 | 85.5 | 71.8 |
| 94 | 105.5 | 101.3 | 94.6 | 96.5 | 84.7 |
| 95 | 98.7 | 101.5 | 93.6 | 91.8 | 70.4 |
| 96 | 108.9 | 120.6 | 92.2 | 100.2 | 76.3 |
| 97 | 101.3 | 96.0 | 96.9 | 85.0 | 67.7 |
| 98 | 112.3 | 127.3 | 92.8 | 82.2 | 31.2 |
| 99 | 109.3 | 124.6 | 94.3 | 91.0 | 58.2 |
| 100 | 110.2 | 116.5 | 85.9 | 88.5 | 73.6 |
| 101 | 103.9 | 109.8 | 91.1 | — | 83.3 |
| 102 | 104.8 | 103.1 | 97.6 | — | 64.0 |
| 103 | 107.9 | 111.7 | 95.8 | — | 78.3 |
| 104 | 113.7 | 115.4 | 111.1 | — | 114.9 |
| 105 | 102.6 | 104.7 | 85.2 | — | 81.8 |
| 106 | 114.5 | 126.9 | 106.4 | — | 48.5 |
| 107 | 105.3 | 109.9 | 92.2 | — | 79.2 |
| 108 | 120.2 | 119.3 | 106.1 | — | 102.9 |
| 109 | 117.2 | 113.0 | 107.7 | — | 113.6 |
| 110 | 118.1 | 123.9 | 92.2 | — | 102.7 |

EXAMPLE 19

Examination of the dose effect

The effect of the different doses of those compounds of formula (I) was examined which showed better results in the previous tests.

The test was carried out in jars with a surface of 120 $cm^2$. A mixture of plowed-land surface soil (humus %=1.82; $pH_{H2O}=6.72$; $pH_{KCl}=6.69$; $K_A=41.2$) as well as sand was used for the test in a ratio of 1:1.

At first 500 g each of the mixture were weighed into the jars, then the seeds of the test plants were sown onto the soil.

maize (*Zea mays*, L) NK-PX-15: 15 corns/jar
sunflower (*Helianthus annuus*): 15 corns/jar
Hungarian grass (*Setaria* sp): 1 g/jar
crowfoot grass (*Echinocloa crus-galli*): 1 g/jar.

Then the seeds were covered with 200 g each of a soil mixture, the chemical treatments were performed in different doses on the soil by spraying. The products of the invention were used in formulation 10 EC (emulsion concentrate). As comparison EPTC as well as product 80 EC containing antidote AD-67 were used for the treatment of the test plants.

After spraying still 100 g each of soil were weighed, then the soil was watered up to a water capacity of 60% and in the course of the cultivation the evaporated water was supplemented by watering on the basis of weight measurement.

The plants were cultivated under 400 W daylight lamps of type HgMI/D. The daily average temperature was 25.8° C. (min. 22.8° C., max. 28.8° C.), the relative humidity 60.7%.

The evaluation was performed by measuring the green mass of the plants as well as the length of sprouts in the case of maize on the 11th day after the treatment.

The test results are set forth in Tables VII and VIII.

TABLE VII

Examination of the dose effect on the sprout length and green weight of maize

| Compounds | Maize sprout length in percent Dose kg/ha active agent 0 | 1 | 2 | 4 | 8 | 16 | Maize green weight in percent Dose kg/ha active agent 0 | 1 | 2 | 4 | 8 | 16 |
|---|---|---|---|---|---|---|---|---|---|---|---|---|
| Number according to Table I No. | | | | | | | | | | | | |
| 3 | 100 | 95.7 | 103.9 | 102.2 | 97.4 | 92.6 | 100 | 95.5 | 110.0 | 100.4 | 100.6 | 92.4 |
| 4 | 100 | 103.5 | 103.5 | 97.4 | 59.7 | 46.3 | 100 | 108.5 | 109.6 | 102.7 | 56.9 | 46.8 |
| 27 | 100 | 99.1 | 97.0 | 92.6 | 82.3 | 55.8 | 100 | 94.9 | 110.5 | 96.9 | 76.9 | 56.5 |
| 28 | 100 | 97.0 | 93.9 | 81.0 | 75.3 | 41.6 | 100 | 99.4 | 100.5 | 82.4 | 74.0 | 41.9 |
| 164 | 100 | 90.5 | 70.6 | 96.1 | 93.1 | 92.6 | 100 | 91.5 | 84.7 | 94.4 | 101.1 | 90.0 |
| EPTC + AD-67 | 100 | 95.2 | 90.9 | 96.1 | 95.2 | 81.0 | 100 | 98.0 | 94.2 | 92.7 | 99.3 | 80.1 |

TABLE VIII

| Compounds | Examination of the dose effect on the green weight of sunflowers, crowfoot grass and Hungarian grass — Sunflower green weight in percent dose kg/ha active agent 0 | 1 | 2 | 4 | 8 | 16 | Crowfoot grass green weight in percent dose kg/ha active agent 0 | 1 | 2 | 4 | 8 | 16 | Hungarian grass green weight in percent dose kg/ha active agent 0 | 1 | 2 | 4 | 8 | 16 |
|---|---|---|---|---|---|---|---|---|---|---|---|---|---|---|---|---|---|---|
| No. according to Table I | | | | | | | | | | | | | | | | | | |
| 3 | 100 | 94.2 | 119.1 | 114.2 | 96.6 | 83.8 | 100 | 225.0 | 25.0 | — | — | — | 100 | 127.0 | 103.3 | 51.2 | 15.6 | — |
| 4 | 100 | 89.0 | 116.1 | 97.4 | 106.0 | 100.2 | 100 | 200.0 | 25.0 | — | — | — | 100 | 64.0 | 74.9 | 4.7 | — | — |
| 27 | 100 | 108.6 | 92.3 | 88.1 | 89.7 | 94.2 | 100 | 150.0 | 125.0 | 60.0 | 10.0 | — | 100 | 55.5 | 15.2 | — | — | — |
| 28 | 100 | 100.5 | 87.3 | 91.4 | 90.5 | 86.4 | 100 | 275.0 | 75.0 | 25.0 | — | — | 100 | 74.4 | 47.4 | — | — | — |
| 164 | 100 | 97.8 | 95.9 | 96.8 | 92.2 | 88.5 | 100 | 300.0 | 100.0 | 40.0 | — | — | 100 | 2.4 | 1.4 | 1.0 | — | — |
| EPTC + AD-67 80 EC | 100 | 80.5 | 84.8 | 94.1 | 86.6 | 76.6 | 100 | 50.0 | — | — | — | — | 100 | — | — | — | — | — |

From tha results of the tests it comes clear that except compound No. 3 of Table I all other compounds control the monocotyledonous weeds even in a dose of 4–8 kg/ha active agent and do not cause harm to maize and sunflowers.

EXAMPLE 20

A test was performed with compounds Now. 1, 3, 4, 13, 27 and 28 according to Table I at 14 different plants. Jars with a surface of 120 $cm^2$ were used in the test series.

For the test carried out in jars plough-land surface soil passed through a sieve with a mesh size of 2 mm (humus %=1.82; $pH_{H2O}$=6.72; $pH_{KCl}$=6.69; $K_A$=41.2) was weighed in a quantity of 400 g per jar, then the seeds of the test plants were sown.

| | | |
|---|---|---|
| 1. Winter wheat (*Triticum aestivum*) | 50 | corns/jar |
| 2. Sugar-beet (*Beta vulgaris*) | 30 | " |
| 3. Rice (*Oryze sativa*) | 50 | " |
| 4. Pea (*Pisum sativum*) | 15 | " |
| 5. Bean (*Phosealus vulgaris*) | 15 | " |
| 6. Pumpkin (*cucurbita pepo*) | 10 | " |
| 7. Melon (*citrullus lanatus*) | 15 | " |
| 8. Millet (*Panikum miliaceum*) | 0.5 | g/jar |
| 9. Sorghum (*Sorghum bicolor*) | 0.5 | " |
| 10. Abutilon (Abutilon sp) | 0.5 | " |
| 11. Flax (*Linum usitatissimum*) | 50 | corns/jar |

-continued

| | |
|---|---|
| 12. Cheese-rennet (*Galium aparina*) | 50 " |
| 13. Rape (*Brassica napus*) | 50 " |
| 14. Heckle-mustard (*Raphanus raphanistrum*) | 50 " |

The seeds are covered with 200 g each of soil, then they were chemically treated with a dose of 3 kg/ha of the indicated compounds as well as product 80 EC containing the EPTC and antidote AD-67. Then still 100 g each of soil were weighed immediately and the soil was watered up to a water capacity of 60% and the uniform soil wetness was ensured by repeated watering in the course of the cultivation.

The plants were cultivated under 400 W daylight lamps of type HgMI/D. The daily average temperature was 24.7° C. (min. 21.5° C., max. 27.7° C.) and the relative humidity 63.1%.

The evaluation was performed by measuring the green weight of the plants on the 13th day after the treatment when the results were related to the untreated control the value of which was taken as 100%.

The test results are set forth in Tables IX and X.

TABLE IX

| Plants | Selectivity concerning cultivated plants — Compounds according to Table I: 1 | 3 | 4 | 13 | 27 | 28 | EPTC + AD-67 EC |
|---|---|---|---|---|---|---|---|
| winter wheat | 69.9 | 71.8 | 66.0 | 90.3 | 35.9 | 62.1 | — |
| sugar-beet | 88.1 | 92.1 | 17.8 | 90.1 | 92.1 | 92.1 | 83.2 |
| rice | 73.9 | 82.6 | 65.2 | 65.2 | 78.2 | 56.5 | — |
| pea | 39.1 | 50.8 | 112.3 | 107.7 | 145.5 | 144.0 | 24.0 |
| bean | 83.2 | 98.4 | 78.8 | 102.7 | 79.9 | 89.1 | 85.9 |
| pumpkin | 74.6 | 85.4 | 87.8 | 81.9 | 110.3 | 87.7 | 79.5 |
| melon | 102.7 | 85.7 | 90.2 | 109.2 | 95.3 | 80.9 | 38.5 |

TABLE X

| Plants | Selectivity concerning weeds — Compounds according to Table I: 1 | 3 | 4 | 13 | 27 | 28 | EPTC + AD-67 80 EC |
|---|---|---|---|---|---|---|---|
| millet | 142.5 | — | 10.3 | 47.3 | — | — | — |
| sorghum | 22.7 | 20.3 | 12.5 | 67.2 | — | 13.3 | 6.2 |
| abutilon | 100.9 | 77.4 | 66.9 | 97.2 | 168.0 | 72.6 | 24.5 |
| flax | 89.9 | 84.8 | 94.9 | 97.5 | 110.1 | 58.2 | 52.0 |
| cheese-rennet | 233.0 | — | 133.0 | 100.0 | 66.7 | 106.7 | — |
| rape | 84.6 | 83.3 | 62.8 | 137.2 | 80.8 | 92.3 | — |
| heckle-mustard | — | — | — | — | — | — | — |

From our tests we determined that successful weed-control can be performed with the products according to the invention without causing any harm to cultivated plants.

We claim:

1. A compound selected from the group consisting of
(a) N-methyl-N-(N′-ethyl-acet-anilido)-S-ethylthiolcarbamate;
(b) N-ethyl-N-(N′-methyl-acet-anilido)-S-ethylthiolcarbamate;
(c) N-ethyl-N-(N′-ethyl-acet-anilido)-S-ethylthiolcarbamate;
(d) N-allyl-N-(N′-ethyl-acet-anilido)-S-ethylthiolcarbamate;
(e) N-ethyl-N-(N′-methyl-acet-anilido)-S-n-propylthiolcarbamate; and
(f) N-ethyl-N-(N′-ethyl-acet-anilido)-S-n-propylthiolcarbamate.

2. A herbicidal composition which comprises 10 to 80% by weight of the compound as defined in claim 1; 10 to 90% by weight of a solid or liquid diluting agent; and 1 to 30% by weight of a surface active agent.

3. The herbicidal composition defined in claim 2 wherein the liquid diluting agent is present in an amount of 20 to 90% by weight and is a solvent not miscible with water.

4. The herbicidal composition defined defined in claim 2 wherein the solid diluting agent is an artifical amorphous silicic acid or minerals of the silicate, sulfate type, said solid diluting agent present in an amount of 20 to 90% by weight.

5. The herbicidal composition defined in claim 2 wherein the surface active agent is present in an amount of 1 to 15% by weight.

6. The herbicidal composition defined in claim 2 wherein the surface active agent is a cationic, anionic, or nonionic tenside.

7. A method of controlling the growth of monocotyledonous or dicotyledonous weeds at a plantsite which comprises the step of applying to said plantsite a herbicidally effective amount of the herbicidal composition defined in claim 2.

* * * * *